US008828047B2

(12) United States Patent
Bissinger et al.

(10) Patent No.: US 8,828,047 B2
(45) Date of Patent: Sep. 9, 2014

(54) FORCEPS WITH PRESSURE REGULATION

(75) Inventors: Guenter Bissinger, Teningen (DE); Matthias Bissinger, Emmendingen (DE); Jochen Hein, Emmendingen (DE)

(73) Assignee: Guenter Bissinger Medizintechnik GmbH, Teningen (DE)

( * ) Notice: Subject to any disclaimer, the term of this patent is extended or adjusted under 35 U.S.C. 154(b) by 323 days.

(21) Appl. No.: 12/589,791

(22) Filed: Oct. 28, 2009

(65) Prior Publication Data

US 2010/0137901 A1 Jun. 3, 2010

(51) Int. Cl.
*A61B 17/00* (2006.01)
*A61B 17/30* (2006.01)
*A61B 19/00* (2006.01)

(52) U.S. Cl.
CPC ........... *A61B 17/30* (2013.01); *A61B 2019/304* (2013.01)
USPC ........................................................ 606/206

(58) Field of Classification Search
USPC ................. 606/205–211; 433/159; 30/29, 30/173–175; 294/99.2; 81/382
See application file for complete search history.

(56) References Cited

U.S. PATENT DOCUMENTS

| 2,181,746 | A | * | 11/1939 | Siebrandt | 606/96 |
| 2,449,521 | A | * | 9/1948 | Warner | 219/161 |
| 2,802,467 | A | * | 8/1957 | McNally | 606/103 |
| 3,253,327 | A | * | 5/1966 | McElligatt | 29/741 |
| 3,465,621 | A | * | 9/1969 | Ladd | 294/99.2 |
| 3,638,516 | A | * | 2/1972 | Wondowski | 294/99.2 |
| 3,752,017 | A | * | 8/1973 | Lloyd et al. | 81/9.44 |
| 4,257,406 | A | * | 3/1981 | Schenk | 600/219 |
| 4,375,218 | A | * | 3/1983 | DiGeronimo | 606/52 |
| 4,461,297 | A | * | 7/1984 | Sutter | 606/210 |
| 4,898,161 | A | * | 2/1990 | Grundei | 606/105 |
| 5,047,046 | A | * | 9/1991 | Bodoia | 606/205 |
| 5,122,139 | A | * | 6/1992 | Sutter | 606/51 |
| 5,385,471 | A | * | 1/1995 | Chuen | 433/153 |
| 5,653,729 | A | * | 8/1997 | Chappuis et al. | 606/207 |
| 5,735,857 | A | * | 4/1998 | Lane | 606/99 |
| 5,893,853 | A | * | 4/1999 | Arnold | 606/133 |
| 6,110,171 | A | * | 8/2000 | Rydell | 606/51 |
| 6,322,363 | B1 | * | 11/2001 | Beecher et al. | 433/159 |
| 6,663,616 | B1 | * | 12/2003 | Roth et al. | 606/1 |
| 7,431,721 | B2 | * | 10/2008 | Paton et al. | 606/51 |
| 7,513,897 | B2 | * | 4/2009 | Sutter et al. | 606/51 |
| 8,152,213 | B2 | * | 4/2012 | Fortune | 294/99.2 |
| 2005/0107825 | A1 | * | 5/2005 | Lee | 606/210 |
| 2005/0234447 | A1 | * | 10/2005 | Paton et al. | 606/51 |
| 2010/0092918 | A1 | * | 4/2010 | Muller et al. | 433/159 |
| 2013/0018412 | A1 | * | 1/2013 | Journey et al. | 606/206 |

* cited by examiner

*Primary Examiner* — Darwin Erezo
*Assistant Examiner* — Amy Shipley
(74) *Attorney, Agent, or Firm* — Collard & Rose, P.C.

(57) ABSTRACT

The invention relates to a forceps with two branches which can be pushed resiliently against each other, are connected to each other at one end by means of a connection section and have a resilient section distally adjoining the connection section, a grip section distally adjoining the resilient section and forceps legs distally adjoining the grip section. In order to afford the possibility of matching the spring force of the forceps to different operational aims, provision is made according to the invention for a support apparatus which is arranged on a branch in the region between the connection section and the grip section or in the proximal region of the grip section, which support apparatus extends transversely between the branches in the direction of the other branch and which is adjustable in terms its spacing from the other branch.

6 Claims, 2 Drawing Sheets

Figure 2B:
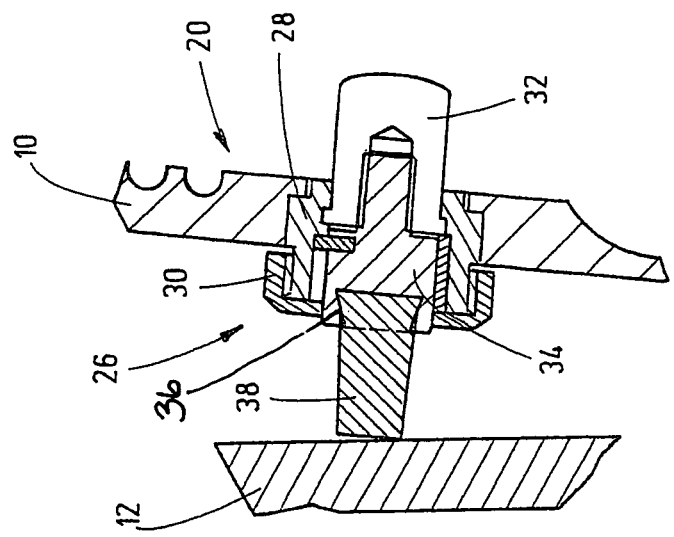

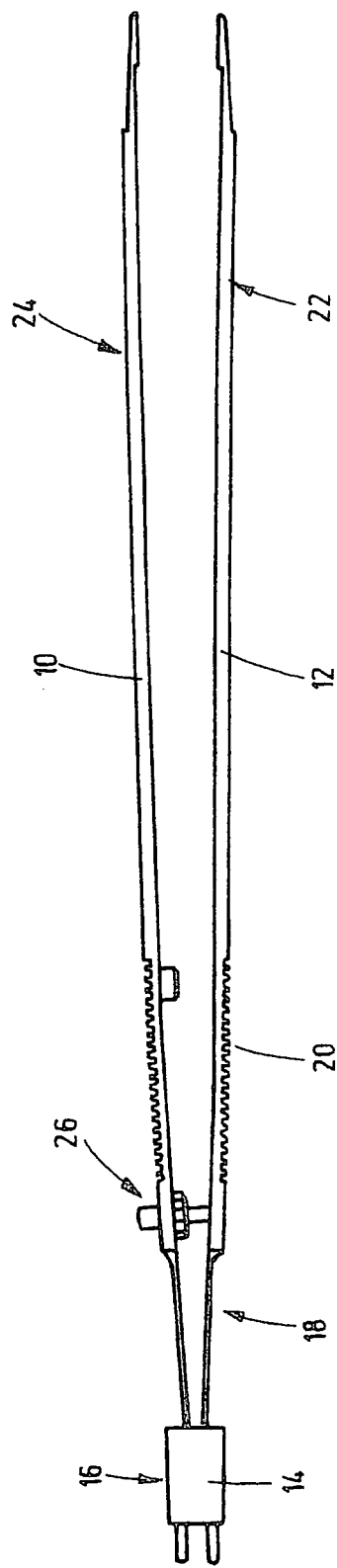
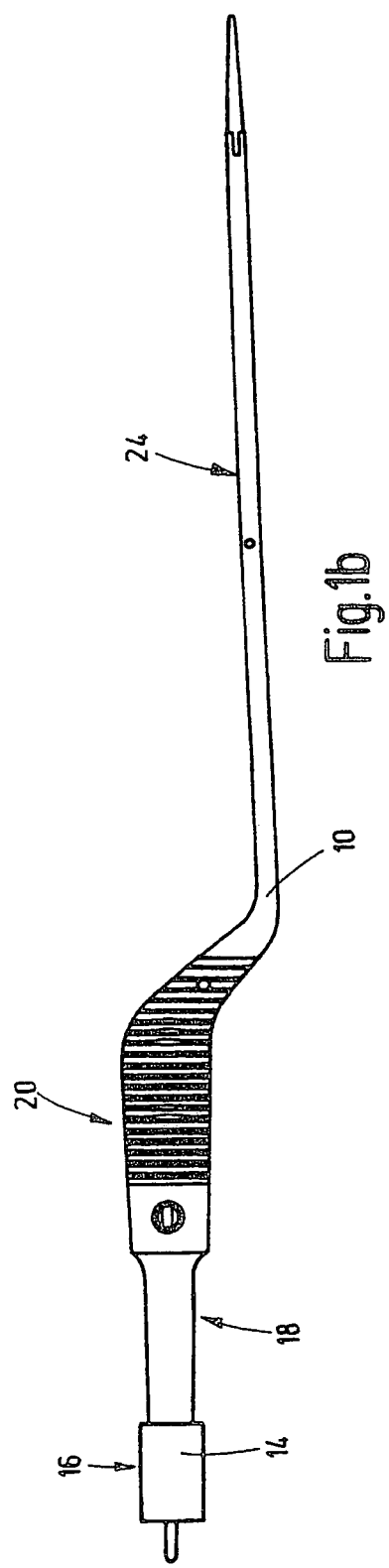

FORCEPS WITH PRESSURE REGULATION

The invention relates to a forceps with two branches which can be pushed resiliently against each other, are connected to each other at one end by means of a connection section and have a resilient section distally adjoining the connection section, a grip section distally adjoining the resilient section and forceps legs distally adjoining the grip section.

This type of forceps is utilized in the most diverse applications, inter alia for the dissection of tissue and vessels. Here, the dissection force was previously determined from the predetermined spring force of the forceps which results from the length, the cross section and material of the forceps spring and which therefore cannot be influenced by the operator. Thus, the desired or required dissection force is often unavailable.

Using this as a starting point, the object of the invention is to provide a forceps of the type mentioned initially in which the spring force can be matched to the respective operational aims.

In order to solve this object, a combination of features as described herein is proposed. Advantageous developments and refinements of the invention are also described herein.

In accordance with the invention, provision is made for a support apparatus which is arranged on a branch in the region of the resilient section or in the proximal region of the grip section, which support apparatus extends transversely between the branches in the direction of the other branch and which is adjustable in terms of its spacing from the other branch. The spring force of the forceps changes depending on how far away the support apparatus is set from the second branch. The change in spacing of the support apparatus from the second branch can for example be effected by a part whose length is adjustable transversely with respect to the branches. Since the resilient section basically has a V-shape, it is also feasible for a support element with a fixed length to be displaced along the one branch. In principle, a combination of these two principles is also possible.

In a preferred refinement of the invention, the support apparatus has an actuation grip which pierces the branch, protrudes outwardly and is used to adjust a support element of the support apparatus. Thus the spring force of the forceps can be changed in particularly simple fashion.

Adjusting the support element can for example be made possible by the support element having a male thread section and being screwed into a corresponding female thread section in the branch or in a housing for the support element arranged on the branch. The housing for the support element can be screwed, pressed and/or adhesively bonded into the branch.

If the forceps is used for electrosurgical purposes, the branches have to be electrically insulated from each other. By way of example, this can be effected by an insulating coating for the branches, at least in the region of the connection section, or by embedding the proximal ends of the branches at a distance from one another in a clamping block. The latter case simplifies the connection of electrical supply lines to the branches. Furthermore, the support element or the housing thereof should also be insulated from at least one of the branches or at least partly be composed of a dielectric material.

Figure 2A:
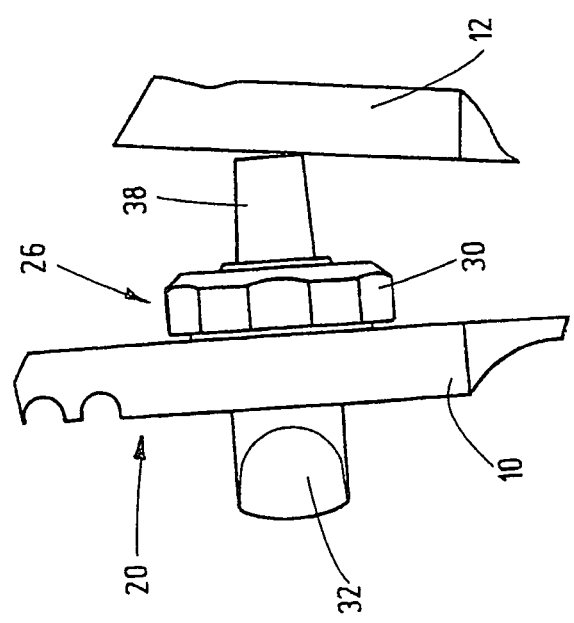

In the following text, the invention will be explained in more detail on the basis of exemplary embodiments illustrated schematically in the drawing, in which FIGS. 1a and b show a plan view and side view of a bipolar forceps with a support element which is arranged on a branch and which can change its spacing from the other branch; and FIGS. 2a and b show an enlarged plan view and side view of the one branch of the forceps in the region of the support element.

The forceps illustrated in the drawing is designed as a bipolar forceps for electrosurgical applications and substantially comprises two branches 10, 12 embedded in a clamping block 14 in the region of a proximal connection section. The clamping block 14 comprises a dielectric but non- or hardly elastic material, for example a hard plastic. Electric contacts of the branches protrude proximally beyond the clamping block. A resilient section 18 distally adjoins the connection section 16 designed in this fashion, said resilient section being adjoined by a grip section 20 and the forceps legs 22, 24 adjoining the latter.

A support apparatus 26 arranged in the proximal region of the grip section 20 comprises a housing with a sleeve 28 made of a dielectric material, for example a plastic or ceramics, and a cap 30 which is designed as a metal lathe part. The cap 30 does not touch the branch 10, that is to say it is insulated therefrom by the sleeve 28. An actuation grip 32 is mounted in the sleeve 28 such that it can rotate but cannot be displaced axially. By means of a female thread, said grip acts on a male thread of a displacement piece 34 as a support element, mounted in a rotationally fixed fashion in the housing, as a result of which the displacement piece 34 is displaced in the longitudinal direction with respect to the housing when the actuation grip 32 is turned; that is to say the opposing branch 12 is approached or moved away from it. The support on the other branch 12 is however not effected directly via the displacement piece 34. In order to avoid pressure points on or damage to the branch 12 or the coating thereof and to distribute the supporting force over a larger area, the displacement piece 34 has an undercut opening 36 on the end face, into which opening a slightly conically shaped silicone plug 38 can be pressed in an interlocking fashion. The silicone plug 38 is pressed flat against the opposing branch when the forceps is closed and thus distributes the force over a larger area. The displacement piece and the silicone plug together form the support element of the support apparatus. In the case of the illustrated forceps, the force region can be adjusted approximately in the ratio 1:2, for example in the range from 800 to 1600 mN.

The cap 30 is screwed onto the sleeve 28 and has on its circumference a milled spanner flat and so the housing can easily be dismantled in the case of contamination or for replacing a component.

In conclusion, the following should be noted: The invention relates to a forceps with two branches 10, 12 which can be pushed resiliently against each other, are connected to each other at one end by means of a connection section 16 and have a resilient section 18 distally adjoining the connection section 16, a grip section 20 distally adjoining the resilient section 18 and forceps legs 22, 24 distally adjoining the grip section 20. In order to afford the possibility of matching the spring force of the forceps to different operational aims, provision is made according to the invention for a support apparatus 26 which is arranged on a branch in the region of the resilient section 18 or in the proximal region of the grip section 20, which support apparatus extends transversely between the branches in the direction of the other branch and which is adjustable in terms of its spacing from the other branch.

The invention claimed is:

1. A forceps with two branches which can be pushed resiliently against each other, are connected to each other at one end via a connection section and have a resilient section distally adjoining the connection section, a grip section distally adjoining the resilient section and forceps legs distally adjoining the grip section, the forceps further comprising a support apparatus which is arranged on one of the branches in the region of the resilient section or in a proximal region of the grip section, which support apparatus extends transversely between the branches in a direction of the other one of the branches and which has a support element that is adjustable in terms of its spacing from the other branch, wherein the support element is pressed against the other branch when the forceps is closed, wherein the support apparatus has an actuation grip which pierces the branch, protrudes outwardly, is used to adjust the spacing of the support element from the other branch, and can rotate but does not displace axially, and wherein the support element has a male thread section and is screwed into a corresponding female thread section in the branch or in a housing for the support element arranged on the branch.

2. The forceps as claimed in claim 1, wherein the housing for the support element is screwed, pressed and/or adhesively bonded into the branch.

3. The forceps as claimed in claim 1, wherein the housing is electrically insulated from at least one of the branches or is composed of a dielectric material.

4. The forceps as claimed in claim 1, wherein the proximal end regions of the branches are embedded at a distance from one another in a clamping block preferably composed of a dielectric material and have connections for an electric current source which proximally protrude beyond the clamping block.

5. The forceps as claimed in claim 1, wherein the actuation grip is configured so that a rotation of the actuation grip towards the other branch displaces the support element to protrude further from the first branch towards the other branch.

6. A forceps with two branches which can be pushed resiliently against each other, are connected to each other at one end via a connection section and have a resilient section distally adjoining the connection section, a grip section distally adjoining the resilient section and forceps legs distally adjoining the grip section, the forceps further comprising a support apparatus which is arranged on one of the branches in the region of the resilient section or in the proximal region of the grip section, which support apparatus extends transversely between the branches in the direction of the other one of the branches and which has a support element that is adjustable in terms of its spacing from the other branch, wherein the support element is pressed against the other branch when the forceps is closed, wherein the support apparatus has an actuation grip which pierces the branch, protrudes outwardly, and is used to adjust the spacing of the support element from the other branch, and wherein the support element is formed from a metal or plastic part with an undercut plug opening facing the other branch and a silicone plug pressed into the plug opening in an interlocking fashion.

* * * * *